United States Patent [19]

Edge, Jr.

[11] 4,155,804
[45] May 22, 1979

[54] REMOVAL OF VOLATILE ORGANIC COMPONENTS FROM SPENT SULFITE EFFLUENT

[75] Inventor: Dexter Edge, Jr., Olympia, Wash.

[73] Assignee: International Telephone and Telegraph Corporation, New York, N.Y.

[21] Appl. No.: 559,174

[22] Filed: Mar. 17, 1975

[51] Int. Cl.² .................... D21C 11/02; D21C 11/10
[52] U.S. Cl. ................................ 162/16; 162/36; 159/47 WL
[58] Field of Search .................... 162/16, 15, 36; 260/347.9; 159/47 WL

[56] References Cited
U.S. PATENT DOCUMENTS

| | | | |
|---|---|---|---|
| 1,838,109 | 12/1931 | Richter | 162/16 |
| 2,801,206 | 7/1957 | Goddard | 162/16 |
| 3,085,038 | 4/1963 | Rovesti | 162/16 |
| 3,462,343 | 8/1969 | Phillips | 162/36 |
| 3,764,462 | 10/1973 | Baierl | 162/16 |

OTHER PUBLICATIONS

Rydholm, S. A., "Pulping Processes", Interscience Publishers, NY, NY, p. 497, (1965).
Casey, J. P., "Pulp & Paper", Sec. Ed., vol. I, Interscience Pub., NY, NY, pp. 158–162, (1960).
ABIPC, vol. 41 #10, 4–71, Abstract #9613, effective date 11-15-70.

Primary Examiner—S. Leon Bashore
Assistant Examiner—William F. Smith
Attorney, Agent, or Firm—J. B. Raden; H. J. Holt

[57] ABSTRACT

Volatile organic components are removed from the effluent liquor of an acid sulfite digestion process by concentrating the effluent liquor in multiple stages to form an organic-rich aqueous fraction, an organic-lean aqueous fraction and a high solids content fraction, continuously withdrawing the organic-lean and high solids content fraction from the recovery process, continuously recycling the organic-rich fraction to the digestion step to form a closed loop which acts to build up the concentration of volatile organic components, and continuously separating and withdrawing from the closed loop the bulk of the volatile organic components in a stream more concentrated than that of the closed loop.

10 Claims, 1 Drawing Figure

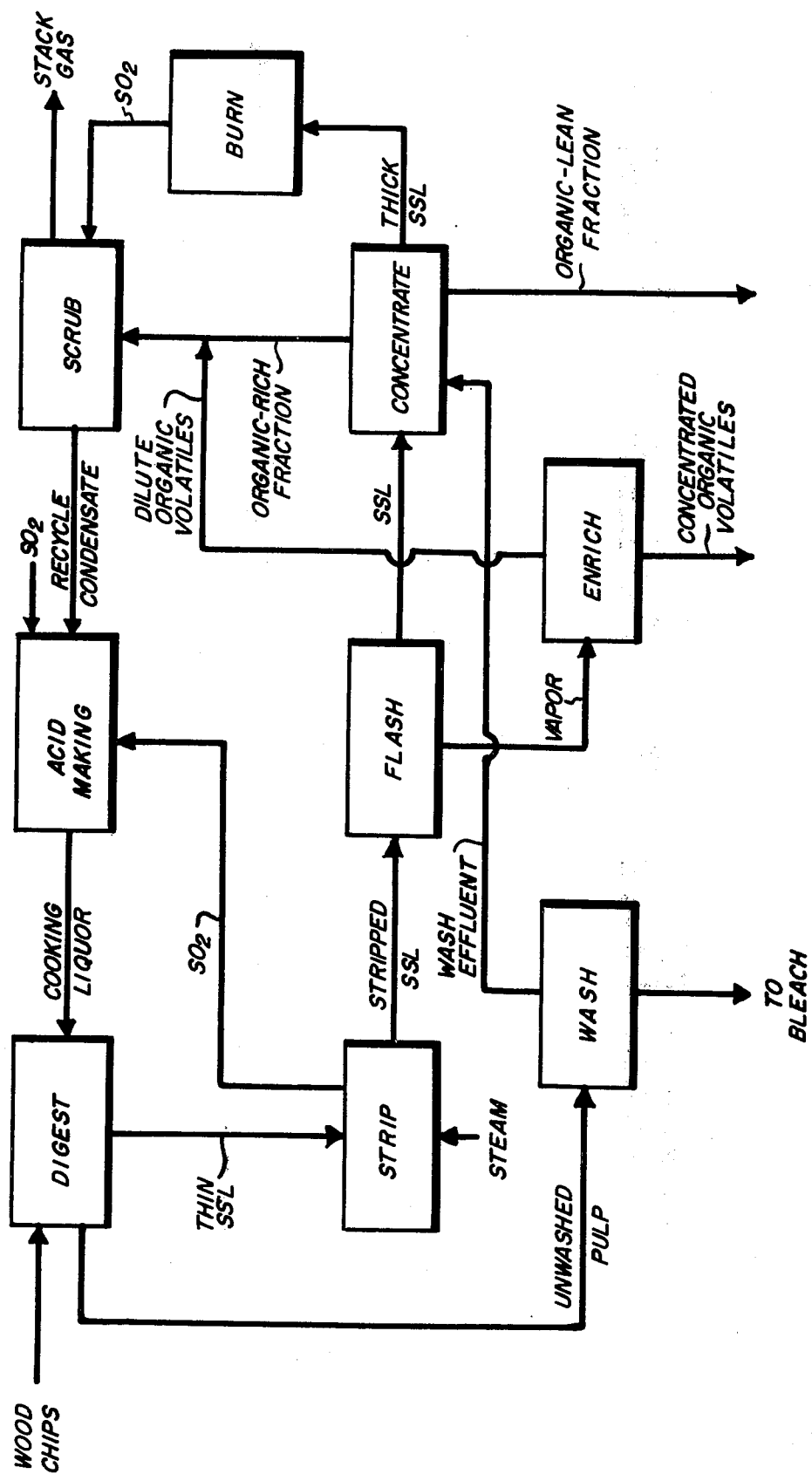

REMOVAL OF VOLATILE ORGANIC COMPONENTS FROM SPENT SULFITE EFFLUENT

This invention relates to a recovery process for the acid sulfite digestion of wood and in particular to such a process in which volatile organic components are continuously recycled and removed from the spent sulfite effluent stream.

Modern pulp mills must evaporate and burn spend cooking liquors in order to avoid gross polution. Burning has long been the practice of kraft pulp mills for economic reasons but only in recent years has burning been employed in sulfite mills to reduce polution. It is known that a large number of volatile organic compounds are formed in pulping wood by the sulfite process. During evaporation of the spent cooking liquor to remove water and raise the solids content to a level which permits burning, the volatile organic compounds are carried over into the condensate. Contrary to expectations, little of the volatile organic compounds are burned. It is calculated that substantial amounts, on the order to 80–90%, of the volatile organic compounds remain in the liquid effluent from the mill.

The main volatile compounds of consequence in the effluent are methanol, acetic acid and furfural. Of these, furfural is of particular concern because of its toxicity to aquatic life. We have found that the organic materials in the effluent other than the volatile organic components do not build up extensively if the effluents are reused or recycled to the cooking liquor. This is because such other organic materials have low volatility or decompose during subsequent passes through the digestor. However, efforts to find an economical physical or chemical treatment of evaporator condensate to remove volatile organic components have proven unsuccessful.

It is accordingly a primary object of the present invention to provide an economical process for the removal of volatile organic components from the effluents of sulfite pulping processes.

It is a more specific object of this invention to provide a process for the substantial removal of furfural and methanol from sulfite mill effluents.

It is still an additional object of this invention to provide a process for the substantial removal of volatile organic components from such effluents without the necessity for secondary treatment.

The foregoing and other objects of the invention are achieved by concentrating the effluent liquor from the acid sulfite digestion of wood in multiple stages to form an organic-rich aqueous fraction, an organic-lean aqueous fraction and a high solids content fraction, continuously withdrawing the organic-lean and high solids content fraction from the recovery process, continuously recycling the organic-rich fraction to the digestion step to form a closed loop which acts to build up the concentration of volatile organic components, and continuously separating and withdrawing from the closed loop the bulk of the volatile organic components in a stream more concentrated than that of the closed loop.

The process of the present invention provides a relatively simple but effective means of removing two major toxic contaminants — methanol and furfural — from the liquid effluent of sulfite mills. The process has little effect on acetic acid because the latters' volatility is so close to that of water. However, one of the surprising results of the present invention, is the finding that acetic acid, as well as formic acid, other organic acids and furfural may be recycled to the cooking liquor without adversly affecting pulp quality. Formic acid, present in small amounts in spent sulfite liquor (SSL), has been repeatedly reported in the literature as a cause of decomposition of the cooking liquor leading to "burnt cook". While the reasons for the absence of adverse affect on pulp quality are not fully understood, it is believed that the recycled formic acid in the present process is destroyed in the digester. The literature has also indicated a requirement for additional base in the cooking liquor to compensate for recycled acetic and other acids. It has been found that the concentrations of free and combined $SO_2$ are not greatly changed during cooking by the presence of these recycled acids in the present process. Thus, contrary to literature reports, I have found that the foregoing components of the SSL may be recycled to the digester with little or no effect on pulp quality.

All of the commercially proven processes for the recovery of spent sulfite liquor from sodium, ammonium, and magnesium based sulfite pulping processes consist of evaporation of the SSL followed by incineration in one of a variety of furnaces. In the present invention, these steps of the SSL recovery process may be carried out in essentially known fashion. Accordingly, detailed descriptions of these aspects of the recovery process and of the overall sulfite pulping process will not be here repeated except to the extent that they are necessary to an understanding of the invention. Complete descriptions of the acid sulfite digestion processes may be found, for example, in *Pulping Processes*, Rydholm, Interscience Publishers, 1965 at pages 439–576 and of sulfite recovery processes at pages 764–835 of this text. These portions of the Rydholm text are hereby incorporated by reference.

The invention will be better understood by the following description which should be considered together with the accompanying drawing in which the single FIGURE illustrates in simplified form a flow diagram of the process.

Wood chips and sulfite cooking liquor are fed to the digester. The cooking liquor is a sodium, ammonium or magnesium-base acid sulfite liquor, that is, sulfite liquor containing an excess of $SO_2$. Upon completion of the cooking operation, pressure in the digester is relieved and the cooking liquor is pumped from the digester. The pulp is then washed with water to remove most of the spent sulfite liquor. The washed pulp is sent to subsequent bleaching stages.

The thin SSL from the digesters is fed to a continuous steam stripper where a high proportion of the $SO_2$ is removed and returned to the acid making system. Such a stripping operation is well known and may be carried out in conventional fashion. It is shown, for example, in U.S. Pat. No. 2,710,254. The stripped SSL is then passed to a flash tank to relieve the pressure to atmospheric. The flashed vapor contains a substantial quantity of volatile organic material which is sent to an organic-enrichment column, where the SSL vapor is separated into a concentrated fraction containing the bulk of the volatile organic components and a dilute fraction. The concentrated fraction is withdrawn from the recovery loop while the dilute fraction may either be sewered or combined with the other condensates recycled through the scrubber. By "concentrated" as used herein with reference to the stream withdrawn from the recycle loop is meant a stream having a substantial content of volatile organic components and containing, on a weight basis, a many-fold higher percentage of volatile organic components than the dilute stream from which it is separated and which remains in the loop for eventual recycle to the digester.

The exact point in the cycle for the enrichment step where the bulk of the volatile organic components are removed from the SSL stream is unimportant. The bulk of the volatile organic materials could also be removed at other portions of the cycle, as for example, from the organic-rich fraction by stripping or other means. A convenient means of accomplishing the enrichment step in which the bulk of the volatile organic components are separated and removed is in a fractionating column or tower in which the vapor is separated into various fractions having differing boiling points. By condensing the tower overhead-vapor stream and refluxing a portion of the condensed liquid to the top of the fractionating column, further concentration of the volatile organic materials is obtained. Such fractionating columns are well known and are used, for example, in commercial furfural plants.

The remainder of the SSL from the flashing step and the effluent from the washing step are fed continuously to an evaporation system where the effluent is concentrated in multiple stages to form an organic-rich aqueous fraction, an organic-lean aqueous fraction and a high solids content fraction. In the evaporation process, most of the volatile organic materials are vaporized and thus appear in the evaporator condensate. The remaining volatile organic components in the high solids content thick SSL is burned in the furnace, or otherwise withdrawn from the recovery process. The more volatile of the volatile organic materials, methanol and furfural, appear principally in the condensate from certain portions of the evaporation stages, whereas the acetic acid appears fairly uniformly throughout the entire condensate. The condensates with the principal portions of methanol and furfural form the organic-rich portion and are recycled to the acid-making system via a flue-gas scrubber which servces as the first stage of the acid-making operation. From there, these condensates are recycled to the digester. The remaining condensate, forming the organic-lean portion, is withdrawn from the process and sewered or used elsewhere in the mill as process water.

In place of evaporation, it is possible to use other methods for performing at least a portion of the concentration of the SSL effluent. Freezing or reverse osmosis, for example, could initially remove a substantial portion of the water. If freezing were to be used, the organic-lean fraction would be essentially pure water and the entire condensate from evaporation would then be the organic-rich fraction to be recycled to the acid-making system. As used herein, "organic-rich" and "organic-lean" fractions identify effluent streams from the evaporator or from other concentration means which contain concentrations of volatile organic components both normally relatively low but differing by many fold. The organic-rich condensate will usually contain 4–6 or more times greater concentration by weight of furfural and methanol than the organic-lean condensate, which will usually contain less than 1% of these components.

The configuration of the evaporators is unimportant to the practice of the invention. It is only necessary to select the condensates having the largest concentration of volatile organics for recycle. The evaporation system may, for example, consist of a combination of two vapor-recompression evaporators and a triple-effect evaporator in series. Such evaporators are well known and are currently in use in pulping processes. In such a system, organic-rich condensate from the first vapor recompression evaporator and from the multiple-effect evaporator is collected and recycled while organic-lean condensate from the second vapor-recompression evaporator is withdrawn for disposal or reuse elsewhere in the mills. In mills having only multiple-effect evaporators, it is possible to separate the organic-rich and organic-lean fractions by combining condensates from certain effects. For example, with a sextuple-effect evaporator, condensate resulting from condensation of vapors from the first three liquor effects and the final liquor effect can be collected for recycle, with the condensate from the remaining effects being drawn off for disposal or reuse. The reason for this is that, in addition to the furfural formed during cooking, a small additional amount of furfural is formed during evaporation, particularly under the higher concentration and temperature conditions occuring in the last liquor effect. Thus, lower overall sewering of furfural would occur if condensate from the fourth and fifth effect vapors is sewered rather than condensates from fifth and sixth effect vapors.

The separation of the higher concentration, organic-rich condensates does not in itself afford a practical means of removing the volatile organic materials from the system since the concentrations in these condensate fractions are still quite low — although higher than the remaining fractions. However, if these organic-rich fractions of evaporator condensate are continuously recycled to the cooking liquor for reuse in digestion, the concentration of volatile organic components will increase in the effluent to a level at which they may be readily separated and withdrawn from the system for disposal or recovery as a by-product.

Both of the effluent separation steps — the initial removal of the bulk of the volatile organic components and the subsequent separation by evaporation or other forms of concentration into organic-rich and organic-lean fractions — are essential to the successful use of the process of the invention. Material-balance calculations indicate that use of either of the steps alone will not yeild the same level of reduction in effluent toxicity. In only the initial bulk removal step is carried out, calculations indicate that 54 percent of the furfural would remain in the liquid effluents, if combined condensates are recycled but not split into organic-rich and organic-lean fractions. If the organic-rich fraction is recycled but the bulk removal step is omitted, it is calculated that 59 percent of the furfural would remain in the liquid effluents. By combining the two steps, as little as 20 to 25 percent of the furfural remains in the effluents.

The following example illustrates the practice of the invention. Percentages are by weight.

EXAMPLE 1

160,000 lb./hr. of wood chips are digested in an ammonia-base acid sulfite cooking liquor containing 0.65% combined sulfur dioxide and 7.0% free sulfur dioxide. Test results indicate the following rates of formation of volatile organic components from the cooking operation: 920 lb./hr. of furfural (858 lb./hr. is generated in the digesters, 62 lb/hr. is generated in the multiple-effect evaporators), 1009 lb./hr. of methanol and 4627 lb./hr. of acetic acid. Upon completion of the cooking operation, pressure in the digester is relieved by venting gases back into the cooking acid preparation system. This is done to avoid losses of sulfur dioxide which would otherwise be experienced if the digesters were vented into an open stack. The digester vent gases also contain a portion of aforementioned volatile organic components.

After pumping the spent cooking liquor from the digester, the digested chips are flushed out using part of the cool filtrate from the pulp-washing system. The pulp is next washed with water by passing through a series of countercurrent washing stages. This serves to remove a substantial part (95% or more) of the spent cooking liquor. The washed pulp is sent to subsequent bleaching stages. Only minor amounts of the volatile organic components remain with the pulp leaving the last washing stage, namely: 23 lb./hr. of furfural, 22 lb./hr. of methanol and 117 lb./hr. of acetic acid.

Spent sulfite liquor from the digester is fed to the top of a continuous stripping column. Sufficient steam is introduced into the bottom of this column to insure removal of a high percentage of the residual free sulfur dioxide. The overhead stream, containing the stripped sulfur dioxide also contains some of the volatile organic components along with some uncondensed steam. This stream is also returned to the acid-making system.

Stripped spent sulfite liquor is next passed to a flash tank to relieve the pressure to atmospheric. A considerable quantity of water vapor flashes from the liquor as a result of this reduction in pressure. The flashed vapor also contains a substantial quantity of the volatile organic materials. This vapor is conducted to an organic-enrichment fractionating column. Two streams are taken off the fractionating column — a stream of concentrated organic volatiles and a second dilute stream containing a substantially lower concentration of furfural and methanol. The enriched stream of concentrated organic volatile withdrawn from the fractionating column contains 549 lb./hr. of furfural, 439 lb./hr. of methanol, and 6.2 lb./hr. of acetic acid. The concentration of furfural is 20%, of methanol is 16%, and of acetic acid is 0.23 in the concentrated stream. At this point, the concentrated organic volatiles are withdrawn from the loop. A second dilute stream from the fractionating column, which may be combined with other condensates recycled through the scrubbers, contains 81 lb./hr. of furfural, 196 lb./hr. of methanol and 613 lb./hr. of acetic acid in a concentration of 0.15%, 0.37% and 1.1% respectively, in the dilute stream.

Two SSL streams are fed to the evaporation system, the next step of the recovery process: the stream of unvaporized SSL from the flashing step and the wash effluent from the pulp washing system. The SSL stream from the flashing step contains 564 lb./hr. of furfural (0.13%), 554 lb./hr. of methanol (0.13%) and 4830 lb./hr. of acetic acid (1.1%). The wash effluent contains 632 lb./hr. of furfural (0.13%), 598 lb./hr. of methanol (0.13%) and 3167 lb./hr. of acetic acid (0.66%). (Percentages are percentages by weight in the stream.) These streams are fed continuously to an evaporation system consisting of 2 vapor recompression evaporators and a triple-effect evaporator. In passing through these units in series, the spent liquor concentration is raised from about 10% spent liquor solids to 50% or higher for feed to the recovery furnace. In the evaporation process, most of the remaining volatile organic materials are vaporized and thus appear in evaporator condensate. The remaining amount in the thick sulfite liquor to be burned in the furance amounts to 12 lb./hr. of furfural (0.007%), 0.6 lb./hr. of methanol (0.0004%) and 1223 lb./hr. of acetic acid (0.73%). In the evaporation process, the more volatile components, methanol and furfural, appear largely in the evaporator condensate from the first evaporation stages whereas the acetic acid appears fairly uniformly distributed throughout the entire condensate. The later organic-lean condensates containing the lowest concentrations of furfural and methanol, are sewered or used elsewhere in the mill. In this manner, the amounts going to the sewer (eventually) are 195 lb./hr. of furfural (0.053%), 177 lb./hr. of methanol (0.048%) and 3228 lb./hr. of acetic acid (0.87%). The organic-rich portion of the condensate is recycled to the acid making system via a flue-gas scrubber which serves as the first stage of acid-making operation. This unit is used to remove and recover sulfur dioxide from the recovery furnace stack. Combustion gases from the furnace (after reclaiming heat by generating steam) are sent to the flue gas scrubber. The organic-rich condensate from the evaporators contain 1052 lb./hr. of furfural (0.25%), 974 lb./hr. of methanol (0.23%) and 3544 lb./hr. of acetic acid (0.86%). In the flue gas scrubber, the gases are cooled by direct contact with water and are next contacted by a recirculating solution of ammonium sulfite-bisulfite in a multiple-stage contactor. Makeup ammonium hydroxide is added to this recirculating stream and the aforementioned evaporator condensate is added for dilution water. A small part of the volatile organic materials are stripped from condensate by flue gas and escape from the stack along with small amounts of sulfur dioxide and water vapor. The amounts of organic materials in this exit gas stream are 141 lb./hr. furfural, 370 lb./hr. of methanol and 52 lb./hr. of acetic acid. The balance of the organic material is retained in the ammonium bisulfite solution which is recycled to the scrubber. A portion of this recycle stream is withdrawn for preparing new cooking acid. Additional sulfur dioxide is added to this stream in a series of steps to produce strong cooking acid for the digestion process. Inasmuch as volatile organic materials are present in the cooking acid recycled to the digesters, the amount of volatile organics leaving the digester in the spent sulfite liquor is larger than the aforesaid amount generated during digestion. Because of this buildup from recycling, the concentration levels throughout the system increase substantially, and at many points achieve levels several times larger than would have occurred without recycle. It is this higher concentration which makes possible the economical removal of organics via the enrichment tower.

The following table summarizes the losses of furfural and methanol from various points in the effluent stream of an operation carried out in accordance with the foregoing example. The results have been calculated by computer on the basis of material balances for a full scale mill operation. The lbs./hr. figures in the table are the amounts of the organic volatile components in the digester. The various points in the stream for the amounts and percentages of furfural and methanol losses are labeled in accordance with their identification in the Example. The percentages are of the total formation/hour of furfural and methanol.

|   | Furfural | | Methanol | |
|---|---|---|---|---|
|   | lb/hr | % of Furfural | lb/hr | % of MeOH |
| 1. With Washed Pulp | 23 | 2.5 | 22 | 2.2 |
| 2. Concentrated Organic Volatiles | 549 | 59.7 | 439 | 43.5 |
| 3. Thick SSL Burned | 12 | 1.3 | 1 | 0.1 |
| 4. Organic-Lean Condensate | 195 | 21.2 | 177 | 17.5 |
| 5. Stripped from Condensate by Flue Gas | 141 | 15.3 | 370 | 36.7 |
| TOTAL | 920 | 100 | 1009 | 100 |

The foregoing Table indicates that a substantial portion of furfural and methanol is either destroyed or is removed in a form which renders them reusable; only a minor portion of these components enter the effluent stream.

The process of the invention enables reuse of approximately two thirds of the available evaporator condensate in the preparation of new cooking liquor. The remaining one third may be sewered or used elsewhere in the mill. It is estimated that a major fraction — 75 to 85% — of the methanol and furfural generated in the mill can be withdrawn in concentrated form by use of the present process. The third major volatile organic component — acetic acid — is not removed, but, as indicated previously, its presence does not impair pulp quality. Its removal may be accomplished if desired by known techniques, which may be used in conjunction with the invention without difficulty. One such technique is suppressing the volatility of acetic acid by pre-neutralizing the SSL before evaporation. The acetic acid would then be destroyed in the recovery furnace along with the evaporated thick liquor.

An important advantage of the invention is its adaptability to present sulfite pulp mill recovery systems. It avoids the necessity of costly secondary treatment of evaporator condensates to permit discharge to the sewer or reuse. Rather than treating the condensates to be sewered, the process substantially eliminates the presence of toxic components in the sewered fraction of condensate.

I claim:

1. A recovery process for the removal of volatile organic components from the effluent liquor of the acid sulfite digestion of wood comprising:
concentrating the effluent liquor in multiple stages to form an organic-rich aqueous fraction, an organic-lean aqueous fraction and a high solids content fraction,
continuously withdrawing the organic-lean and high solids content fraction from the recovery process,
continuously recycling the organic-rich fraction to the digestion step to form a closed loop which acts to build up the concentration of the volatile organic components,
and continuously separating and withdrawing from the closed loop the bulk of the volatile organic components in a stream more concentrated than that of the closed loop.

2. The recovery process of claim 1 in which the effluent is of an ammonia-base acid suflite digestion process.

3. The recovery process of claim 1 in which the volatile organic components removed from the effluent liquor are furfural and methanol.

4. The recovery process of claim 1 in which the concentration step comprises evaporation of the effluent passed in series through said multiple stages, certain of said stages providing a condensate of the organic-rich fraction, the other of said stages providing a condensate of the organic-lean fraction.

5. The recovery process of claim 1 in which the continuous separation and withdrawal of the bulk of the volatile organic components comprises passing a portion of said effluent through a fractionating column in which the effluent is separated into two fractions, the first of which is concentrated relative to the other in said volatile organic components, said fractions being withdrawn from the closed loop in separate streams.

6. A recovery process for the removal of volatile organic components consisting essentially of furfural and methanol from the effluent liquor of the acid sulfite digestion of wood comprising:
evaporating the effluent liquor in series through multiple stages, certain of said stages providing an organic-rich condensate, the other of said stages providing an organic-lean condensate,
continuously withdrawing the organic-lean condensate from the recovery process,
continuously recycling the organic-rich condensate to the digestion step to form a closed loop which acts to build up the concentration of the volatile organic components,
and continuously passing a portion of said effluent through a fractionating column in which the effluent is separated into two fractions, the first of which is concentrated relative to the other in said volatile organic components, said first fraction being withdrawn from the closed loop to remove the bulk of the volatile organic components.

7. The recovery process of claim 6 in which said other less concentrated fraction separated in said fractionating column is recycled to said closed loop.

8. The recovery process of claim 6 in which said other less concentrated fraction separated in said fractionating column is withdrawn from the closed loop.

9. The recovery process of claim 6 in which the effluent is steam stripped prior to evaporation to remove the bulk of the $SO_2$ contained in the effluent.

10. The recovery process of claim 9 in which the effluent is flashed subsequent to steam stripping, the flashed vapor being passed to said fractionating step, the remaining effluent from said flashing step being passed to said evaporation step.

* * * * *